United States Patent [19]

Aoki

[11] 4,436,390

[45] Mar. 13, 1984

[54] OPHTHALMIC INSTRUMENT HAVING A CROSS CYLINDER LENS

[75] Inventor: Mitsugu Aoki, Tokyo, Japan

[73] Assignee: Tokyo Kogaku Kikai Kabushiki Kaisha, Japan

[21] Appl. No.: 347,898

[22] Filed: Feb. 11, 1982

[30] Foreign Application Priority Data

Feb. 16, 1981 [JP] Japan .............................. 56-20300[U]
Feb. 27, 1981 [JP] Japan .............................. 56-26962[U]

[51] Int. Cl.$^3$ .............................................. A61B 3/02
[52] U.S. Cl. ..................................... 351/234; 351/235
[58] Field of Search ................. 351/233, 234, 235, 236

[56] References Cited

U.S. PATENT DOCUMENTS

3,498,699 3/1970 Wilkinson .
3,698,799 10/1972 Pitchford .
3,860,330 1/1975 Persson .

Primary Examiner—John K. Corbin
Assistant Examiner—Rodney B. Bovernick
Attorney, Agent, or Firm—Brumbaugh, Graves, Donohue & Raymond

[57] ABSTRACT

An ophthalmic instrument having a cylindrical test lens and a cross cylinder lens which are adapted to be placed in an examining optical path. The cross cylinder lens is mounted on a lens tube which is rotatably mounted on a swingable lever about a pivot axis. A gear train is provided between the lens tube for the cross cylinder lens and a rotatable part for rotating the cylindrical test lens so that the cylinder axis of the cylindrical lens be rotated about the optical axis of the examining optical path by rotating the lens tube.

9 Claims, 13 Drawing Figures

OPHTHALMIC INSTRUMENT HAVING A CROSS CYLINDER LENS

The present invention relates to ophthalmic instruments having cross cylinder means. More particularly, the present invention relates to a mechanism for interconnecting the cross cylinder means and a cylindrical test lens.

In an ophthalmic instrument having a plurality of spherical and cylindrical lenses which are adapted to be selectively placed solely or in combination with other lenses in the optical path so as to let a patient observe a test chart through the lens or lenses which are placed in the optical path for measuring the refractive power of the patient's eye, it has been well known to adopt a cross cylinder device for precise measurements of the astigmatic refractive power and the astigmatic axis of the patient's eye. The cross cylinder device includes a cross cylinder comprised of a pair of cylindrical lenses respectively having a positive and negative refractive powers of the same value and combined with each other with their cylindrical axes crossing perpendicularly to each other. The cross cylinder lens has an intermediate axis which is defined as an axis equally dividing the angle made by the two cylindrical axes and is arranged in the optical path with the intermediate axis aligned with the cylindrical axis of a cylindrical test lens.

A patient observes a test chart through the cross cylinder lens and the cylindrical lens and the cross cylinder lens is rotated about the intermediate axis by an angle of 180° while the patient is observing the chart. If there is any difference between the visions of the chart before and after the rotation of the cross cylinder, the cross cylinder lens is rotated about the optical axis together with the cylindrical lens until the difference between the visions before and after the rotation is eliminated. The axis of the cylindrical lens at this position is aligned with one of the astigmatic axes of the patient's eye.

It will therefore be understood that in the precise measurement of the astigmatic axis, it is necessary to rotate the cross cylinder lens and the cylindrical lens together with the intermediate axis of the cross cylinder lens and the cylindrical axis of the cylindrical lens aligned with each other. The U.S. Pat. No. 3,498,699 discloses a mechanism adapted for such purpose. The mechanism includes a planetary gear mechanism comprised of a sun gear adapted to be rotated by an operating knob and a pair of planetary gears which are in meshing engagement with the sun gear and constitute gear trains for transmitting the rotation of the sun gear respectively to the cross cylinder device and the cylindrical lens.

Generally speaking, the alignment between the intermediate axis of the cross cylinder lens and the cylinder axis of the cylindrical lens must be accomplished with a high precision. Therefore, the rotating mechanism for such lenses must also be of a precise one. However, the mechanism as disclosed in the aforementioned U.S. patent is structurally complicated so that a very high precision must be established in the meshing engagement betwen gears in order to obtain a satisfactory alignment between the axes. Further, the known type of mechanism requires a substantial operating force because it has a lot of gears.

Another problem in the known mechanism is in the arrangement of the operating members. As described previously, the cross cylinder lens has to be rotated about the intermediate axis for an angle of 180° and therefore the cross cylinder device must be provided with an operating member for the purpose. However, in the mechanism as disclosed in the aforementioned U.S. patent, the operating member for rotating the cross cylinder lens and the cylindrical lens together about the optical axis is necessarily located apart from the cross cylinder device due to the arrangement of the gear mechanism. Therefore, the two operating members are undesirably located apart from each other. Further, in an ophthalmic instrument having a cross cylinder device, it is desirable to change the refractive power of the cross cylinder lens in accordance with the cylindrical refractive power of the patient's eye, however, in the known mechanism, it is impossible to change the cross cylinder lens.

It is therefore an object of the present invention to provide a simple interconnecting mechanism for an ophthalmic instrument which is adapted for rotating the cross cylinder lens and the cylindrical lens simultaneously about the optical axis for the same angle.

Another object of the present invention is to provide a cross cylinder arrangement in which the cross cylinder lens can be replaced.

According to the present invention, the above and other objects can be accomplished by an ophthalmic instrument comprising cylindrical lens means and cross cylinder means which are adapted to be located in an examining optical path having an optical axis, housing means containing said cylindrical lens means and said cross cylinder means, swingable lever means mounted on said housing means for swingable movement about an axis substantially parallel with said optical axis of the optical path, said cross cylinder means being carried by said swingable lever means so that it can be moved into and out of said examining optical path in response to the swingable movement of the swingable lever means, said cross cylinder means including cross cylinder lens means having an intermediate axis, inner tube means supporting said cross cylinder lens means for rotation about said intermediate axis by an angle of 180° and outer tube means supporting said inner tube means and mounted on said swingable lever means for rotation about an axis parallel with said optical axis, first rotatable disc means coaxial with said axis of swingable movement of said swingable member, first means for interconnecting said outer tube means with said first rotatable disc means so that a rotation of said outer tube means is transmitted to said first disc means, second means for interconnecting said first rotatable disc means with second rotatable disc means which is adapted for rotating said cylindrical lens means about said optical axis so that a rotation of said first means is transmitted to said second disc means. The first means may be comprised of external gear teeth formed on said outer tube means and said first rotatable means may be formed with external gear teeth adapted for engagement with said gear teeth on the outer tube means. Intermediate gear means may be provided between said external gear teeth on the outer tube means and said external gear teeth on the first rotatable disc means. Alternatively, belt-pulley means may be provided between the outer tube means and the first rotatable means. The second means may also be a gear mechanism.

According to the present invention, the interconnection between the cross cylinder means and the cylindrical lens means can be provided by a single gear train so that the structure is very simple as compared with conventional arrangements. Further, the arrangement of the present invention requires less operating force. Index means may be provided in the examining optical path for showing the orientation of the cylinder axis of the cylindrical lens means and the last mentioned gear mechanism may be used for rotating the index means. External index means may also be provided on the first rotatable disc means to show the orientation of the cylinder axis of the cylindrical lens means.

According to a preferable aspect of the present invention, the inner tube means is removably mounted on said outer tube means so that a cross cylinder lens of a desired refractive power. In this instance, one of the inner tube means and the outer tube means is provided with pin means and the other with groove means and cutout means which makes it possible to remove said pin means from the groove means in the axial direction.

The above and other objects and features of the present invention will become apparent from the following descriptions of preferred embodiments taking reference to the accompanying drawings, in which.

Figure 1:
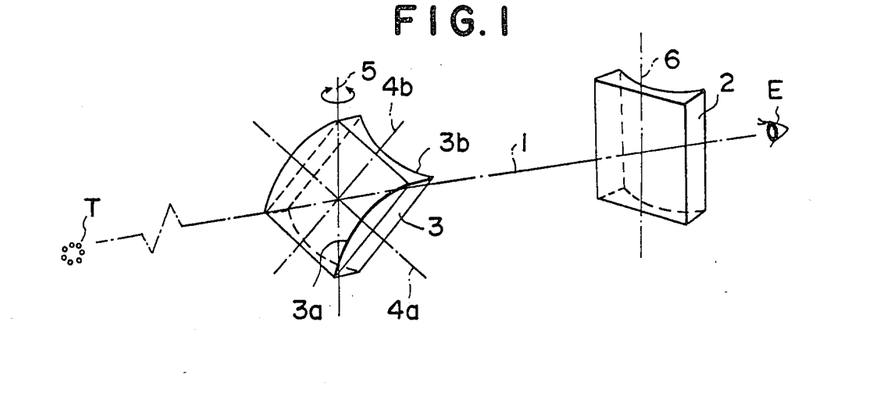
FIG. 1 is a perspective view of the optical system of an ophthalmic instrument having a cross cylinder lens.

Referring now to the drawings, particularly to FIG. 1, there is shown an optical system having a cross cylinder lens for measuring the astigmatic axis. The optical system includes a cylindrical lens 2 and a cross cylinder lens 3 which are disposed along an optical axis 1 of an examining optical path. The patient's eye E observes a target T such as a test chart through the lenses 2 and 3. The cross cylinder lens 3 comprises a positive cylindrical lens element 3a and a negative cylindrical lens element 3b which have cylinder axes 4a and 4b, respectively, directed perpendicularly to each other. The cross cylinder lens 3 has an intermediate axis 5 which is defined by an axis equally dividing the angle made by the axes 4a and 4b. The cylindrical lens 2 is arranged with its cylinder axis 6 aligned with the intermediate axis 5 of the cross cylinder lens 3. In measurement, the cross cylinder lens 3 is rotated by an angle of 180° about the intermediate axis 5 as shown by an arrow to examine as to whether there is any difference between views before and after such rotation. If there is any difference, the cylinder lens 2 and the cross cylinder lens 3 are rotated simultaneously for the same angle about the optical axis 1 to perform a further examination and such operations are repeated until the difference between the views is eliminated.

Referring now to FIGS. 2 through 6, the ophthalmic instrument shown therein includes a lens housing 10 provided with an inspection tube 11. At a side of the tube 11, the housing 10 carries a swingable lever 12 which is mounted thereon at an intermediate portion through a pivot shaft 13. The lever 12 carries a cross cylinder device 14 at one end and a rotary prism 15 of known type at the other end. Through an appropriate rotation of the lever 12, it is possible to put the cross cylinder device 14 and the rotary prism 15 alternately in alignment with the tube 11.

Figure 4:
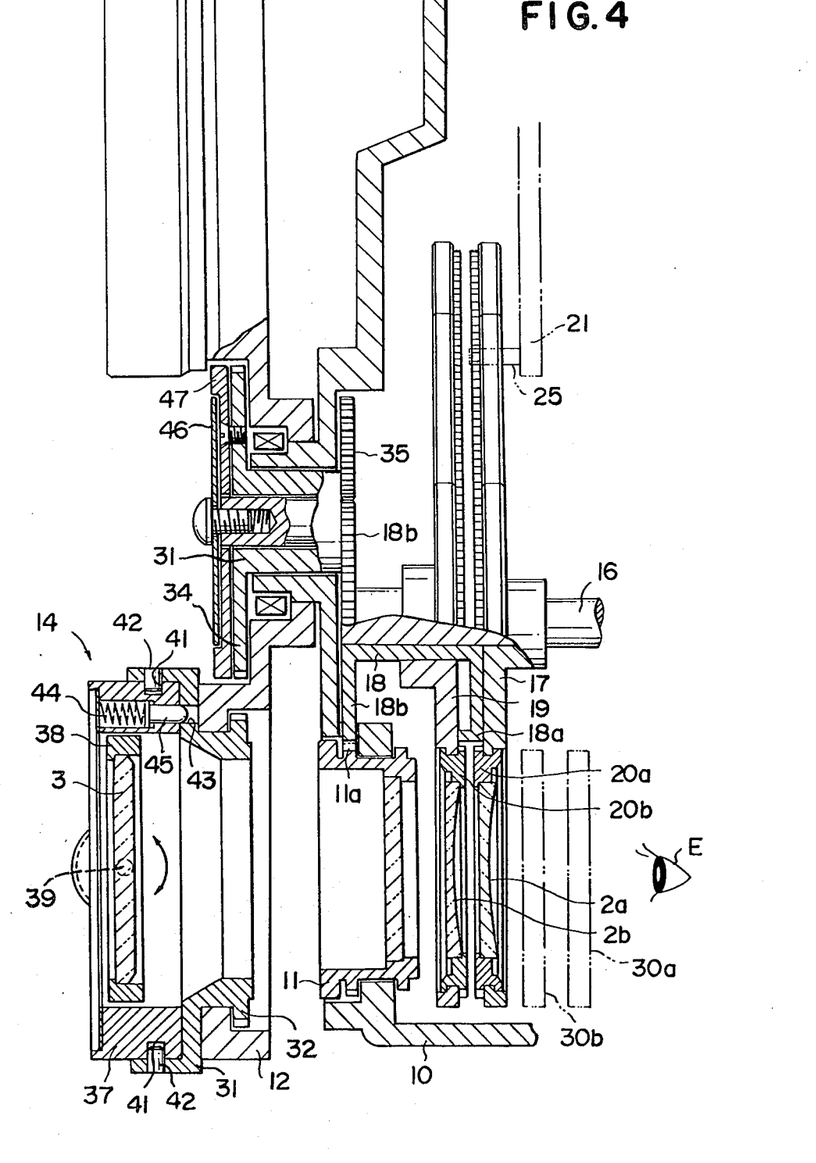
FIG. 4 is an axial sectional view showing the arrangement around the examining optical path.

Referring specifically to FIG. 4, it will be noted that there is provided a support shaft 16 in the housing 10 for rotatably supporting a first lens disc 17 and a gear shaft 18 which has driving gears 18a and 18b. A second lens disc 19 is rotatably supported on the gear shaft 18. The inspection tube 11 is of a substantially cylindrical configuration and carried by the lens housing 10 rotatably about its longitudinal axis. The tube 11 is formed with external gear teeth 11a which are in meshing engagement with the gear 18b so that the inspection tube 11 can be rotated by the gear 18b.

Figure 3:
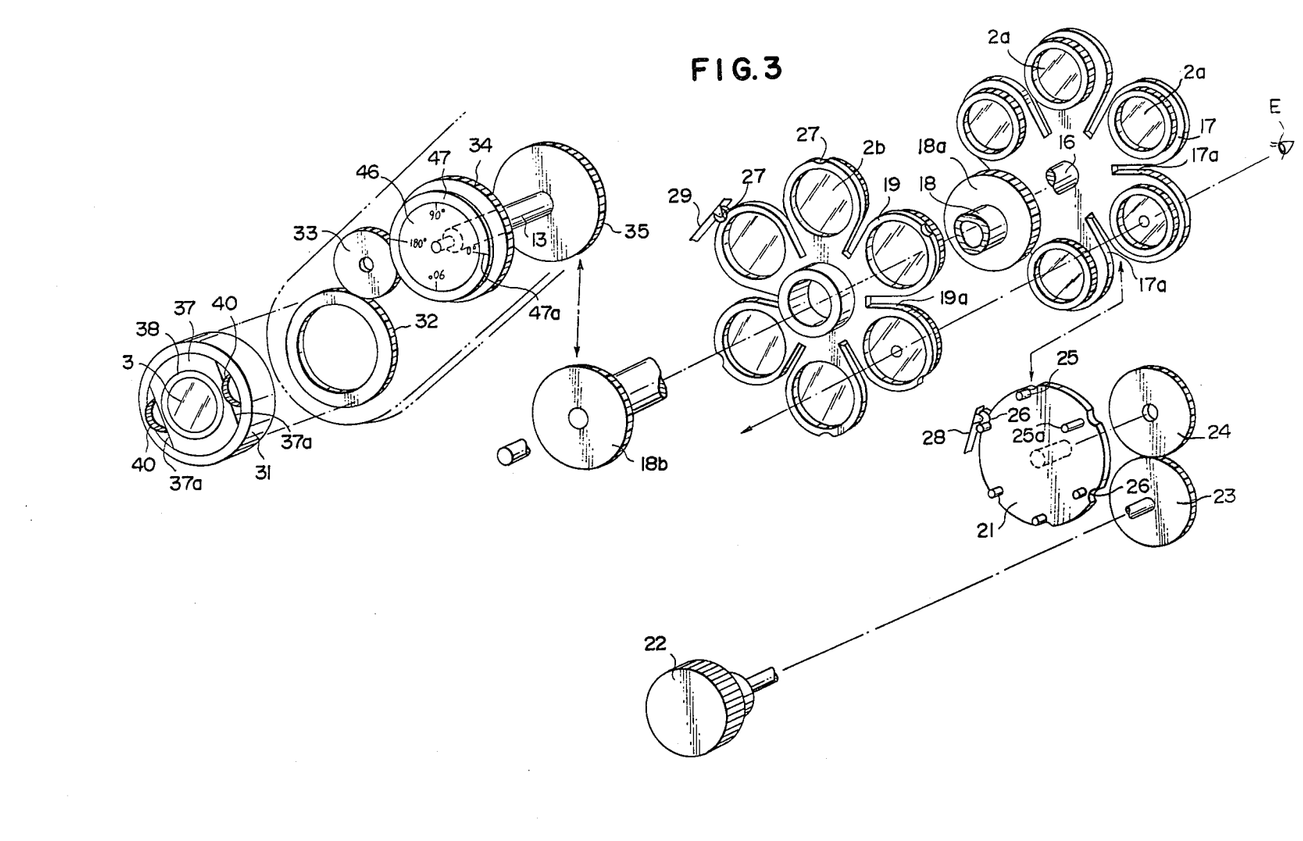
FIG. 3 is an exploded perspective view of the mechanism in the ophthalmic instrument.

The lens discs 17 and 19 are disposed behind the inspection tube 11. As shown in FIG. 3, the first lens disc 17 has a plurality of cylindrical lenses 2a which have different dioptral values and arranged in circumferentially spaced apart relationship. Each of the lenses 2a is mounted rotatably on the disc 17 through a lens frame 20a. Similarly, the second lens disc 19 carries a plurality of cylindrical lenses 2b which are mounted thereon by means of lens frames 20b. The lens frames 20a and 20b have gear teeth which are adapted to be engaged with the gear 18a so that they can be rotated by the gear 18a.

As shown in FIG. 3, the lens discs 17 and 19 have radially directed slots 17a and 17b, respectively, which extend between each two adjacent lenses 2a and 2b. Below the lens discs 17 and 19, there is provided a driving disc 21 which is adapted for driving the lens discs 17 and 19. The driving disc 21 has a gear 24 which is in engagement with a gear 23 having an operating knob 22 so that the disc 21 can be rotated by the knob 22. The driving disc 21 has a plurality of axially extending pins 25 which are located in circumferentially spaced relationship so that the pins 25 are sequentially engaged with the slots 17a in the disc 17 to thereby drive the disc 17 incrementarily to bring one of the lenses 2a on the inspection tube 11.

One of the pins 25, that is, the pin which is designated by the reference numeral 25a has an axial length which is longer than the other pins so that it can engage both the slots 17a and 19b in the discs 17 and 19, respectively. Thus, as the lens disc 17 is incrementarily driven by the driving disc 21, the lens disc 19 is rotated by one step when the lens disc 17 makes a full turn. In order to maintain the lens disc 17 in respective incremental positions, the driving disc is formed at the periphery thereof with circumferentially spaced indentations 26 which are adapted to be engaged with a stopper 28. Similarly, the lens disc 19 is formed with indentations 27 which are adapted for engagement with a stopper 29. Although not shown in the drawings, further lens discs having a plurality of spherical test lenses are provided so that spherical lenses 30a and 30b can appropriately be placed in the optical path.

Referring to FIG. 4, the cross cylinder device 14 includes an outer tube 31 rotatably on the swingable lever 12. The outer tube 31 is provided with an external gear 32 engaged through an idler gear 33 on the lever 12 with a gear 34 provided on the shaft 13 as shown in FIG. 3. On the shaft 13, there is provided a gear 35 which is engaged with the gear 18b on the gear shaft 18. The outer tube 31 constitute an operating knob so that the cylindrical lenses 2a and 2b and the inspection tube 11 can be rotated by the outer tube 31 through the aforementioned gear train. The gears 18a and 18b have the same number of gear teeth and the gear 11a has the same number of teeth as the teeth on the lens frame 20a and 20b so that the inspection tube 11 is rotated simultaneously with the cylindrical lenses 2a and 2b by the same angle. At the front face of the inspection tube 11, there is provided an index 36 which designates the orientation of the cylinder axes of the lenses 2a and 2b.

The cross cylinder device 14 further has an inner tube 37 which is mounted in the outer tube 31. In the inner tube 37, there is a cross cylinder lens 3 which is mounted in a lens frame 38 which is in turn carried by the inner tube 37 for rotation about the intermediate axis of the cross cylinder lens 3 by a pair of mounting pins 39 provided at diametrically opposite positions along the intermediate axis of the cross cylinder lens. The inner tube 37 is formed at diametrically opposite sides confronting to the pins 39 with flat cut-off portions 37a. The pins 39 extend radially outwardly beyond the inner tube 37 and have operating knobs 40 at the outer ends. The inner tube 37 is formed at the outer peripheral surface with a circumferential groove 41 which has a bottom substantially flush with the surfaces of the cutoff portions 37a. The outer tube 31 has a pair of pins 42 which is adapted to be engaged with the groove 41.

Figure 2:
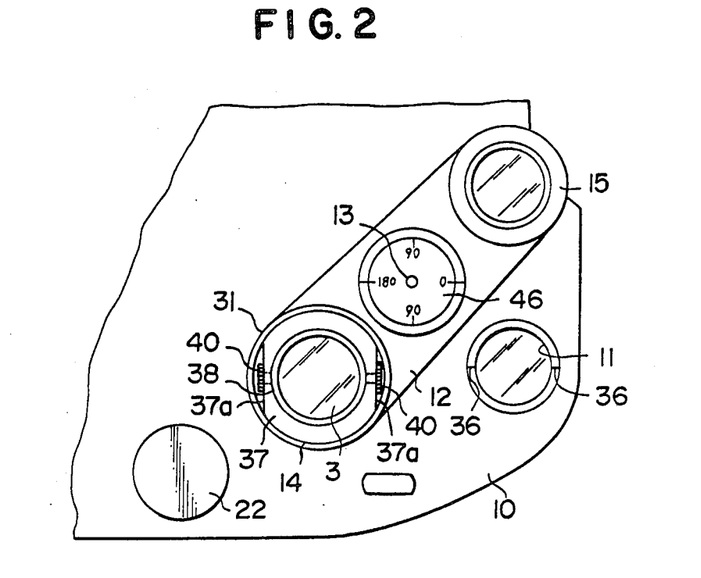
FIG. 2 is a fragmentary front view of an opththalmic instrument showing one embodiment of the present invention.
Figure 5:
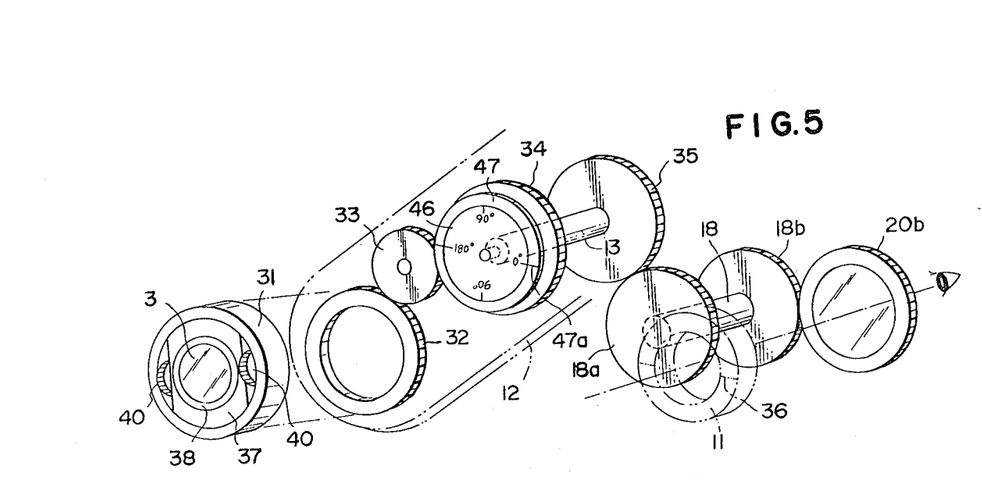
FIG. 5 is a fragmentary perspective view of the mechanism shown in FIG. 3 with the parts in positions for measuring without the cross cylinder lens.
Figure 6:
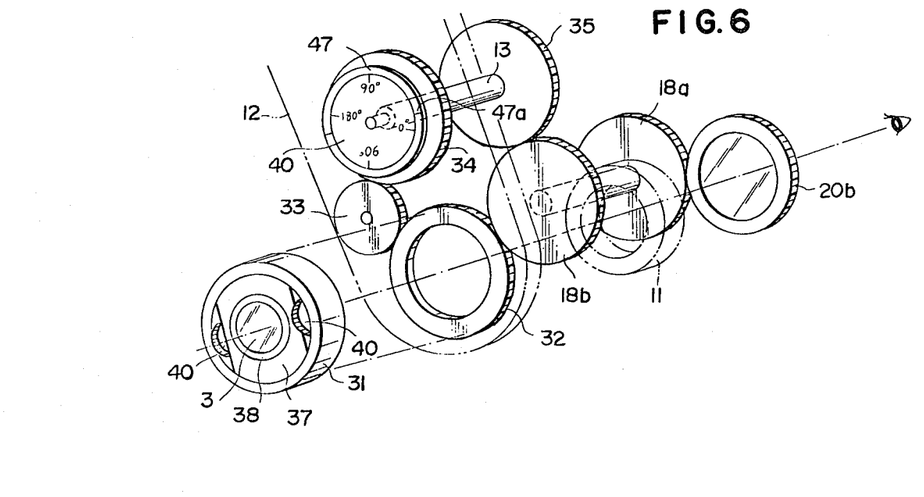
FIG. 6 is a fragmentary perspective view similar to FIG. 5 but showing the cross cylinder located in the optical path.
Figure 7:
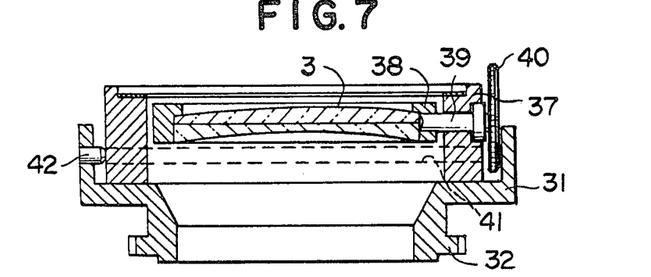
FIG. 7 is an axial sectional view showing one example of the cross cylinder device.
Figure 8:
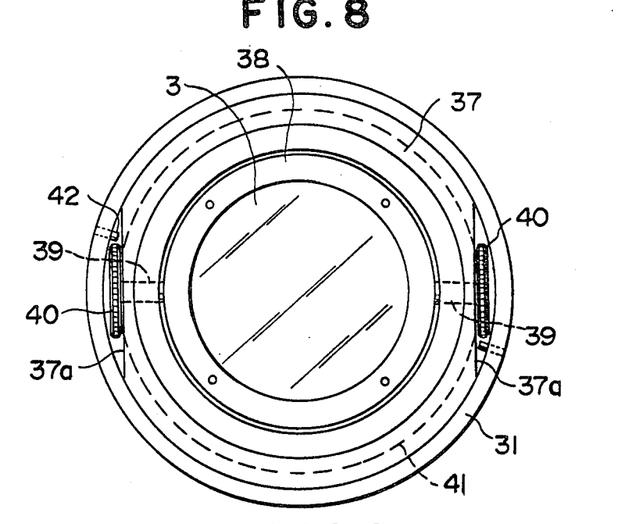
FIG. 8 is a front view of the cross cylinder device shown in FIG. 7.
Figure 9:
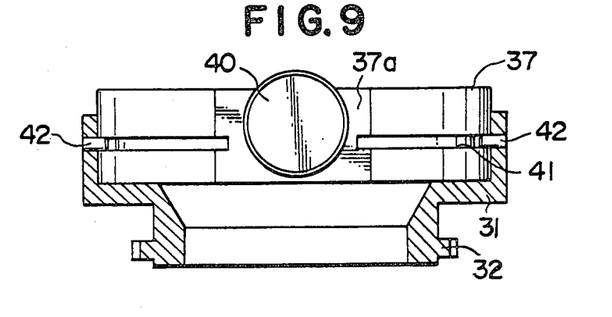
FIG. 9 is a side view of the cross cylinder device with the outer tube cut away to show the inner tube.

The outer tube 31 is formed a the forwardly facing surface with a locating hole 43 and the inner tube 37 has a locating pin 45 which is biased rearwardly by a spring 44 so as to resiliently engage the locating hole 43. Thus, the inner tube 37 can be located by letting the pins 42 on the outer tube 31 engage the groove 41 in the inner tube 37 and rotate the inner tube 37 until the pin 45 is engaged with the locating hole 43. In this position, the intermediate axis of the cross cylinder lens 3 is aligned with the cylinder axes of the cylindrical lenses 2a and 2b.

Where the cross cylinder lens is not to be used in examination, the lever 12 is positioned as shown in FIGS. 2 and 5 so that the cross cylinder device 14 is out of alignment with the inspection tube 11. Even in this position, the cylinder axes of the cylindrical lenses 2a and 2b can be rotated by the outer tube 31 of the cross cylinder device 14. In order to designate the orientation of the cylinder axes in an angular scale, an angular scale disc 46 is provided on the front surface of the lever 12 and the gear 34 is provided with an index plate 47 having an index 47a.

Where the cross cylinder lens is to be used, the lever 12 is swung to the position shown in FIG. 6 so that the cross cylinder device 14 is axially aligned with the inspection tube 11. In this instance, the idler gear 33 on the lever 12 is resolved about the gear 34 while rotating about its own axis. Since the gears 32 and 34 have the same number of teeth, there will be no change in the orientation of the intermediate axis of the cross cylinder lens 3. During examination, the cross cylinder lens 3 is rotated by an angle of 180° through an actuation of the knob 40. The cylinder axes of the cylindrical lenses 2a and 2b and the intermediate axis of the cross cylinder lens 3 can be rotated through an actuation of the cross cylinder device 14.

Where it is desired to replace the cross cylinder lens 3 by another which has a different refractive power, the inner tube 37 is rotated by disengaging the pin 45 from the hole 43 against the action of the spring 44 until the pins 42 are positioned at the cut-off portions 37a as shown in FIG. 8. In this position, the inner tube 37 can be removed from the outer tube 31 together with the cross cylinder lens 3 in the axial direction. The inner tube 37 can be installed on the outer tube 31 by a reverse procedure.

Figure 10:
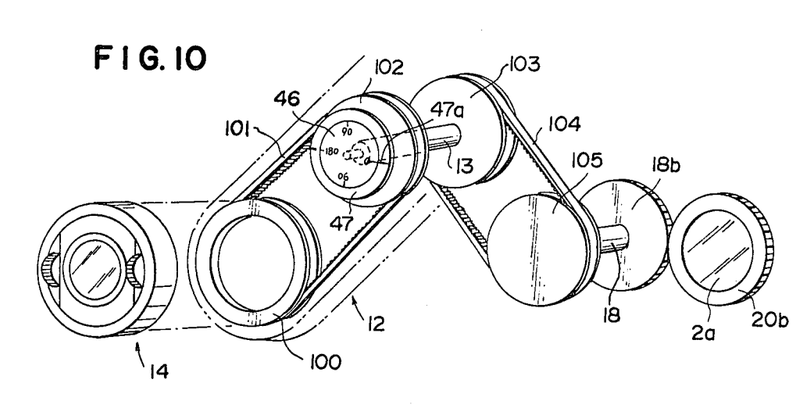
FIG. 10 is a fragmentary perspective view similar to FIG. 5 but showing another embodiment.

Referring now to FIG. 10, there is shown another embodiment of the present invention adopting belt-pulley mechanisms. Thus, in this embodiment, the gears 32, 34, 35 and 18a are substituted by pulleys 100, 102, 103 and 105, respectively. The pulley 100 is secured to the cross cylinder device 14 and has a peripheral groove engaged with a tension belt 101 which is in turn engaged with a peripheral groove of the pulley 102. The pulley 102 is attached with an index plate 47 having an index 47a. The pulley 102 is connected through a shaft 13 with the pulley 103 which is of the same size as the pulley 102. The pulley 103 is engaged with a tension belt 104 which is in turn engaged with the pulley 105. The pulley 105 is connected through a shaft 18 with a gear 18b which is engaged with gear teeth on a lens frame 20b.

Figure 11:
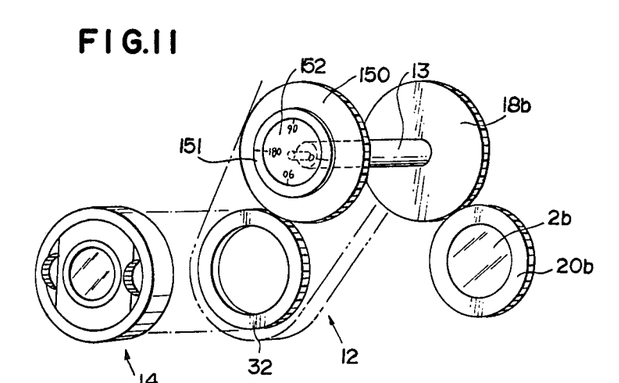
FIG. 11 is a fragmentary perspective view similar to FIGS. 5 and 10 but showing a further embodiment.

Referring to FIG. 11, there is shown a further embodiment in which the gear 32 secured to the cross cylinder device 14 is directly engaged with a gear 150 on the shaft 13. The gear 18b engaged with the gear teeth on the lens frame 20b is mounted on the shaft 13. The cross cylinder device 14 is attached to the gear 32 as in the first embodiment. The gear 150 has the same number of teeth as the gear 18b. The shaft 13 has at its front end an angular scale disc 152 and a stationary index plate 151 is provided to cooperate with the scale disc 152. In this embodiment, the rotaton of the cross cylinder device 14 is transmitted through the gear 32, 150 and 18b to the lens frame 20b. The gear 32 has the same number of teeth as the lens frame 20b so that the rotation of the cylindrical lens 2b is completely synchronized with that of the cross cylinder device 14. The cross cylinder device 14 is arranged so that when the device 14 is positioned coaxial with the optical axis of the optical path, the intermediate axis of the cross cylinder lens is aligned with the cylinder axes of the cylindrical lenses.

Figure 12:
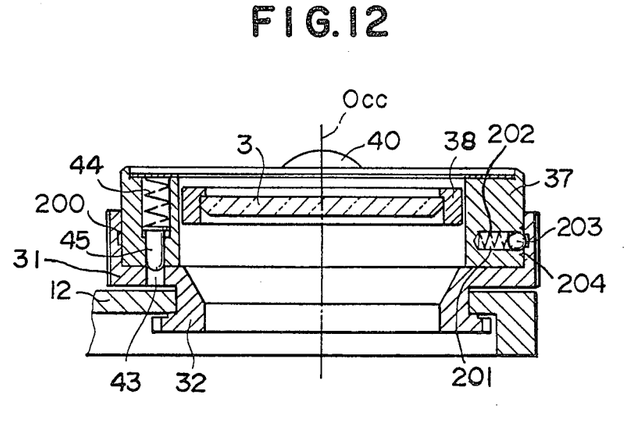
FIG. 12 is an axial sectional view showing another example of the cross cylinder device; and, FIG. 13 is a sectional view similar to FIG. 12 but showing a further embodiment.

In FIG. 12, there is shown another embodiment of the cross cylinder device. In this embodiment, the outer tube 31 is formed at its inner periphery with a circumferential groove 200 and the inner tube 37 with at least one radial hole 201. In the radial hole 201, there is disposed a retaining ball 203 which is spring biased in the radially outward direction by a spring 202 so that it is engaged with the groove 200. At the outer end of the radial hole 201, the material of the inner tube 37 is swaged so that the ball 203 is prevented from falling off the hole 201 as shown by the reference numeral 204. When it is desired to replace the inner tube 37 together with the cross cylinder lens 3, the inner tube 37 is at first rotated about the optical axis Occ to have the pin 45 disengaged from the hole 43. Thereafter, the inner tube 37 is pulled in the axial direction so that the ball 203 is disengaged from the groove 200 against the action of the spring 202. The inner tube 37 can be installed on the outer tube 31 by a reverse operation.

Figure 13:
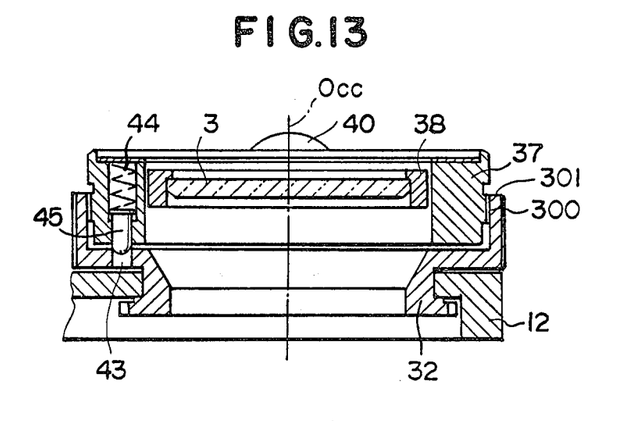

FIG. 13 shows a further embodiment of the cross cylinder device. In this embodiment, the outer tube 32 is formed at the inner peripheral surface with internal screw threads 300 which are engaged with external screw threads 301 formed on the outer peripheral surface of the inner tube 37. Thus, the inner tube 37 can be removed from the outer tube 32 by rotating it to disengage the screw threads 300 from the screw threads 301. The inner tube 37 can be installed on the outer tube 32 by a reverse operation.

The invention has thus been shown and described with reference to specific embodiments, however, it should be noted that the invention is in no way limited to the details of the illustrated structures but changes and modifications may be made without departing from the scope of the appended claims.

I claim:

1. An ophthalmic instrument comprising cylindrical lens means and cross cylinder means which are adapted to be located in an examining optical path having an optical axis, housing means containing said cylindrical lens means and said cross cylinder means, swingable lever means mounted on said housing means for swingable movement about an axis substantially parallel with said optical axis of the optical path, said cross cylinder means being carried by said swingable lever means so that it can be moved into and out of said examining optical path in response to the swingable movement of the swingable lever means, said cross cylinder means including cross cylinder lens means having an intermediate axis, inner tube means supporting said cross cylinder lens means for rotation about said intermediate axis by an angle of 180°, and outer tube means supporting said inner tube means and mounted on said swingable lever means for rotation about an axis parallel with said optical axis, first rotatable disc means coaxial with said axis of swingable movement of said swingable member, first means for interconnecting said outer tube means with said first rotatable disc means so that a rotation of said outer tube means is transmitted to said first disc means, second means for interconnecting said first rotatable disc means with second rotatable disc means which is adapted to rotating said cylindrical lens means about said optical axis so that a rotation of said first means is transmitted to said second disc means.

2. An ophthalmic instrument in accordance with claim 1 in which said first means includes first external gear means formed on said outer tube means and said first disc means includes second external gear means adapted a to be engaged with said first external gear means.

3. An opthalmic instrument in accordance with claim 2 in which intermediate gear means is provided between said first and second gear means.

4. An ophthalmic instrument in accordance with claim 1 in which said second means includes third external gear means rotatable with said first disc means and fourth external gear means formed on said second disc means.

5. An ophthalmic instrument in accordance with claim 1 in which said first means includes belt-pulley means.

6. An ophthalmic instrument in accordance with claim 1 in which said second means includes belt-pulley means.

7. An ophthalmic instrument in accordance with claim 4 in which said fourth gear means is engaged with means for rotating index means which is adapted for designating orientation of cylinder axis of said cylinder lens means.

8. An ophthalmic instrument in accordance with claim 1 in which said first disc means is provided with index means for designating orientation of cylinder axis of said cylindrical lens means.

9. An ophthalmic instrument in accordance with claim 1 in which said inner tube means is removably mounted on said outer tube means.

* * * * *